(12) United States Patent
Kendall et al.

(10) Patent No.: US 6,916,662 B2
(45) Date of Patent: Jul. 12, 2005

(54) PERFORMANCE IMPROVEMENT FOR HEMATOLOGY ANALYSIS

(75) Inventors: Richard G. Kendall, San Jose, CA (US); Thomas V. Schisano, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 108 days.

(21) Appl. No.: 10/355,439

(22) Filed: Jan. 31, 2003

(65) Prior Publication Data

US 2004/0152199 A1 Aug. 5, 2004

(51) Int. Cl.[7] .............................................. G01N 33/86
(52) U.S. Cl. ............................. 436/70; 436/63; 436/66
(58) Field of Search ............................... 436/63, 66, 70

(56) References Cited

U.S. PATENT DOCUMENTS 4,299,726 A * 11/1981 Crews et al. .................. 436/10
4,998,533 A    3/1991 Winkelman
6,225,124 B1 * 5/2001 Houwen et al. ............... 436/63

FOREIGN PATENT DOCUMENTS

| EP | 0 869 347 | 10/1998 |
| WO | 02/097391 | 12/2002 |

OTHER PUBLICATIONS

The PCT Search Report.
Field Learning Center, Hematology Learner, Section 7, Hematology Tests, pp. 44–57.

* cited by examiner

Primary Examiner—Maureen M. Wallenhorst
(74) Attorney, Agent, or Firm—David L. Weinstein (57) ABSTRACT

A method for determining the value of MCV of a fresh sample of blood when the value of MCV for that sample of blood is known, but the period of time that the sample of blood has been stored is not known. The method of this invention allows an automated hematology analyzer to provide a more reliable indication of the initial value of MCV of a sample of blood, i.e., the value of MCV that would have been expected for the sample of blood when the sample was fresh. Furthermore, the method of this invention uses data that is readily available as part of the blood count data.

4 Claims, 6 Drawing Sheets

PERFORMANCE IMPROVEMENT FOR HEMATOLOGY ANALYSIS

BACKGROUND OF THE INVENTION

1. Field of the Invention

This invention relates to a method for analyzing data, and, more particularly, a method for analyzing data relating to hematology test results on aged samples of blood.

2. Discussion of the Art

Automated hematology analyzers are instruments that have been designed to completely automate the analysis of samples of blood. Typically, automated hematology analyzers are used to differentiate the individual blood cells in the samples, count the individual blood cells in the samples, and in some cases, estimate the size of the individual blood cells in the samples. The erythrocyte mean cell volume (hereinafter, alternately, "MCV") is one of the key determinants used in the screening and classification of hematological disease. Automated hematology analyzers have the capability of accurately measuring the value of MCV as part of the blood count. The value of MCV is useful for the primary classification of various disorders of the red blood cells.

It is widely accepted that during storage of samples of blood, the erythrocyte mean cell volume will increase as a function of both time and temperature. Significant changes in the value of MCV can be observed after about 24 hours of storage at room temperature (about 70° C.). These increases can be of sufficient magnitude to result in improper classification of hematology results, thereby resulting in a problem for laboratories that are required to process aged samples of blood. Improper classification of aged samples of blood can lead to such problems as failing to perform follow-up investigations in microcytic patients whose value of MCV has been overestimated, and, consequently, reported to be normal. It is also possible for the value of MCV of a patient to be overestimated when the value of MCV is, in reality, normal, thereby generating unnecessary confirmatory, follow-up tests, which are inappropriate and potentially costly.

In contrast to the erythrocyte mean cell volume, the erythrocyte mean cell hemoglobin (hereinafter, alternately, "MCH") is not subject to changes in the short term (e.g., over a period of several days), because hemoglobin is trapped within the erythrocytes until the cells break down, i.e., undergo hemolysis. In almost all samples of blood, this process of hemolysis does not occur to a significant extent until a number of days after the drawing of the sample.

The relationship between the value of MCV and the value of MCH is generally constant, and is preferably defined by the erythrocyte mean hemoglobin concentration (hereinafter, alternately, "MCHC"). The erythrocyte mean hemoglobin concentration is determined by dividing the erythrocyte mean cell hemoglobin by the erythrocyte mean cell volume (MCHC=MCH/MCV). Because the value of MCV increases as a function of time, the value of MCHC decreases as a function of time. The value of MCHC of a fresh sample of blood is tightly constrained, e.g., typically ranging from about 32 to about 36 g/dl. However, there is a direct correlation between the value of MCH and the value of MCHC. Accordingly, if a sample of blood has been stored and is no longer fresh, it would be desirable to estimate the value of MCV for that sample of blood when it was fresh. Consequently, it is desired to develop a method for using the values of MCH and MCHC of a stored sample of blood to calculate the value of MCV for that sample of blood when that sample of blood was fresh (i.e., before the sample was stored).

In conventional methods in hematology, samples of blood are typically refrigerated to decrease the rate at which the value of MCV increases during storage. While this approach is useful, the conditions demanded are difficult to maintain, especially during such activities as transport from remote facilities.

SUMMARY OF THE INVENTION

In one aspect, this invention provides a method for determining the value of MCV of a fresh sample of blood when the value of MCV for that sample of blood is known, but the period of time that the sample of blood has been stored is not known. The method comprises the steps of:

(a) providing a sample of blood;

(b) determining at least the following hematology parameters of the sample: MCV, MCH, and MCHC;

(c) calculating the theoretical value of MCHC of the sample of blood, the theoretical value of MCHC being the value of MCHC that would have been expected for the sample when the sample was fresh, the theoretical value being derived from the value of MCH;

(d) comparing the theoretical value of MCHC with the value of MCHC determined for the sample of blood; and (e) correcting the value of MCV determined in order to determine the value of MCV for the sample when the sample was fresh.

The method of this invention allows an automated hematology analyzer to provide a more reliable indication of the initial value of MCV of a sample of blood, i.e., the value of MCV that would have been expected for the sample of blood when the sample was fresh. The method of this invention enables one to make a reasonable estimate of the initial value of MCV of a sample of blood, i.e., the value of MCV that would have been expected for the sample of blood when the sample was fresh, even when the duration of storage of the sample and the conditions under which the sample is stored are unknown to the laboratory. Furthermore, the method of this invention uses data that is readily available as part of the blood count data.

BRIEF DESCRIPTION OF THE DRAWINGS

In FIG. 1, each of plots A through K, inclusive, was determined from samples of blood taken from 11 different subjects.

In FIG. 2, each of plots A through K, inclusive, was determined from samples of blood taken from 11 different subjects.

In FIG. 3, each of plots A through K, inclusive, was determined from samples of blood taken from 11 different subjects.

DETAILED DESCRIPTION

As used herein, "MCV" means erythrocyte mean cell volume; "MCH" means erythrocyte mean cell hemoglobin; "MCHC" means erythrocyte mean cell hemoglobin concentration. The parameters MCV, MCH, and MCHC are red blood cell (RBC) count indices. These RBC indices indicate the volume and character of hemoglobin and, consequently, aid in the differential diagnosis of the type of anemia present in a patient. These indices are derived from the measurements of hematocrit, hemoglobin, and red blood cell count. The expression "theoretical value" means the value of a parameter of a sample of blood that is expected to be determined in a sample of fresh blood from a normal patient. The expression "initial value" and the like means the first value of a parameter of a sample of blood determined in a chronological series of determinations of that parameter. The expression "determined value" and the like means the value of a parameter of a sample of blood that is measured and reported by an analytical instrument. The expression "measured value" and the like means the value of a parameter of a sample of blood that is measured and reported by an analytical instrument. The expression "calculated value" means a value of a parameter of a sample of blood that has been determined by a mathematical relationship that utilizes at least one other parameter of the sample of blood and at least one constant. The expression "expected value" means the value of a parameter of a sample of blood that would be expected if the parameter had been determined from the sample when the sample was fresh. The term "aged" means stored for a period of time equal to or greater than 16 hours. The term "fresh", with respect to measurement of a parameter of a sample of blood, means that venipuncture has occurred less than four hours prior to the measurement of the parameter.

According to the method of this invention, the value of MCV of a sample of blood can be calculated by reference to the value of MCH of the sample and the value of MCHC of the sample determined or measured by an analytical instrument. In cases of samples of blood in which the value of MCV measured or determined has increased on account of aging upon storage, the method of this invention enables a more accurate determination of the initial value of MCV of the sample.

Figure 1:
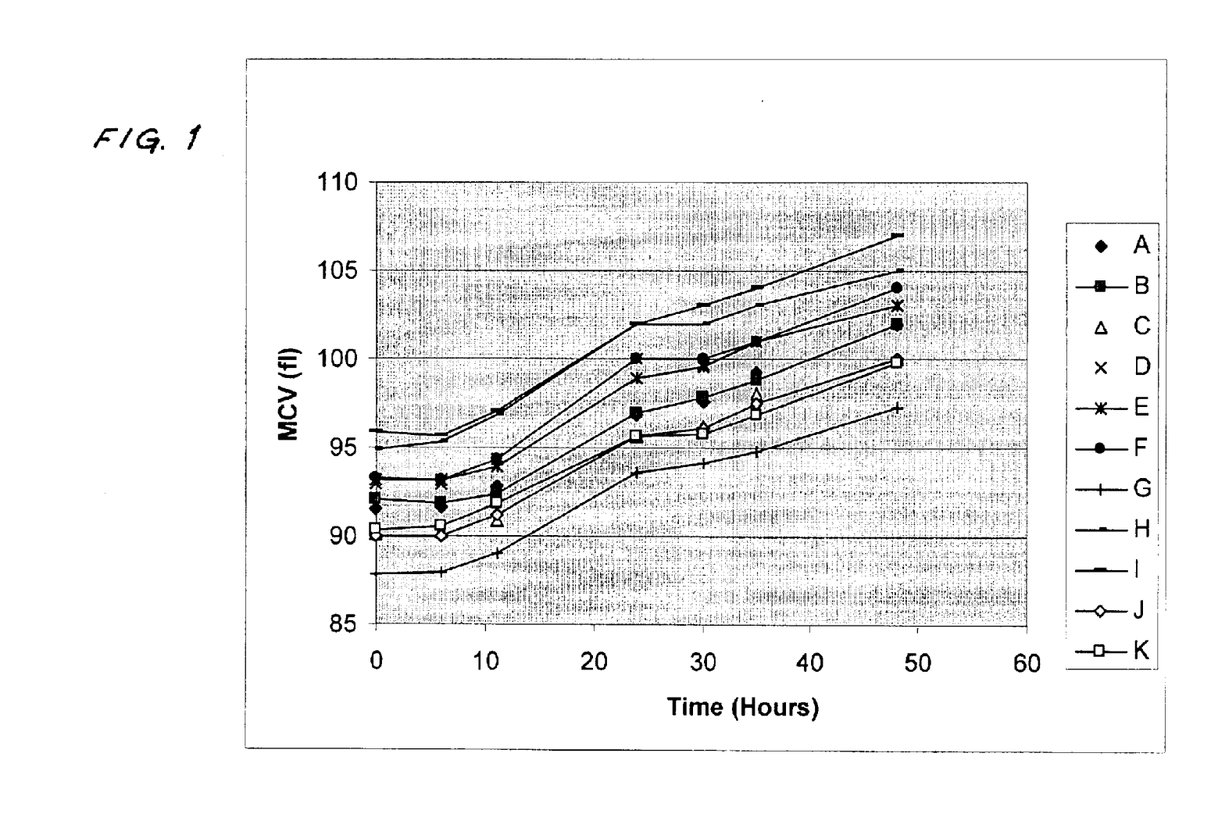
FIG. 1 is a graph showing how the values of MCV of samples of blood determined at given times change as a function of time at room temperature.
Figure 2:
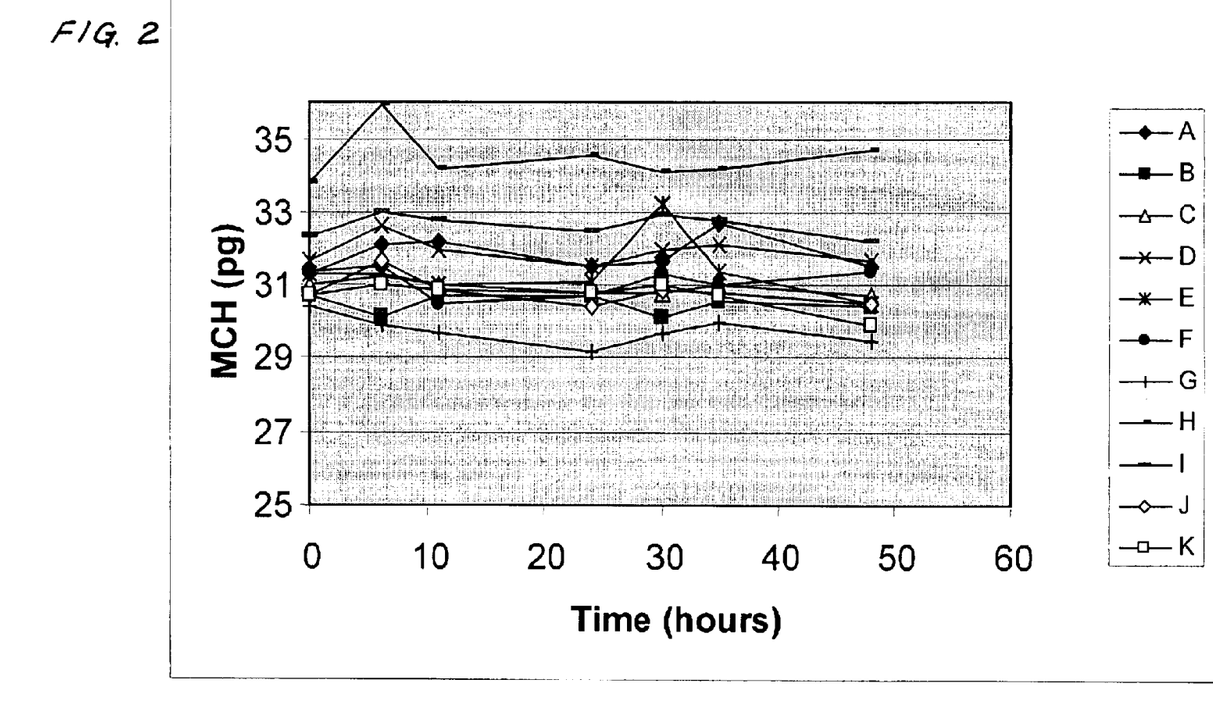
FIG. 2 is a graph showing how the values of MCH of samples of blood determined at given times change as a function of time at room temperature.
Figure 5:
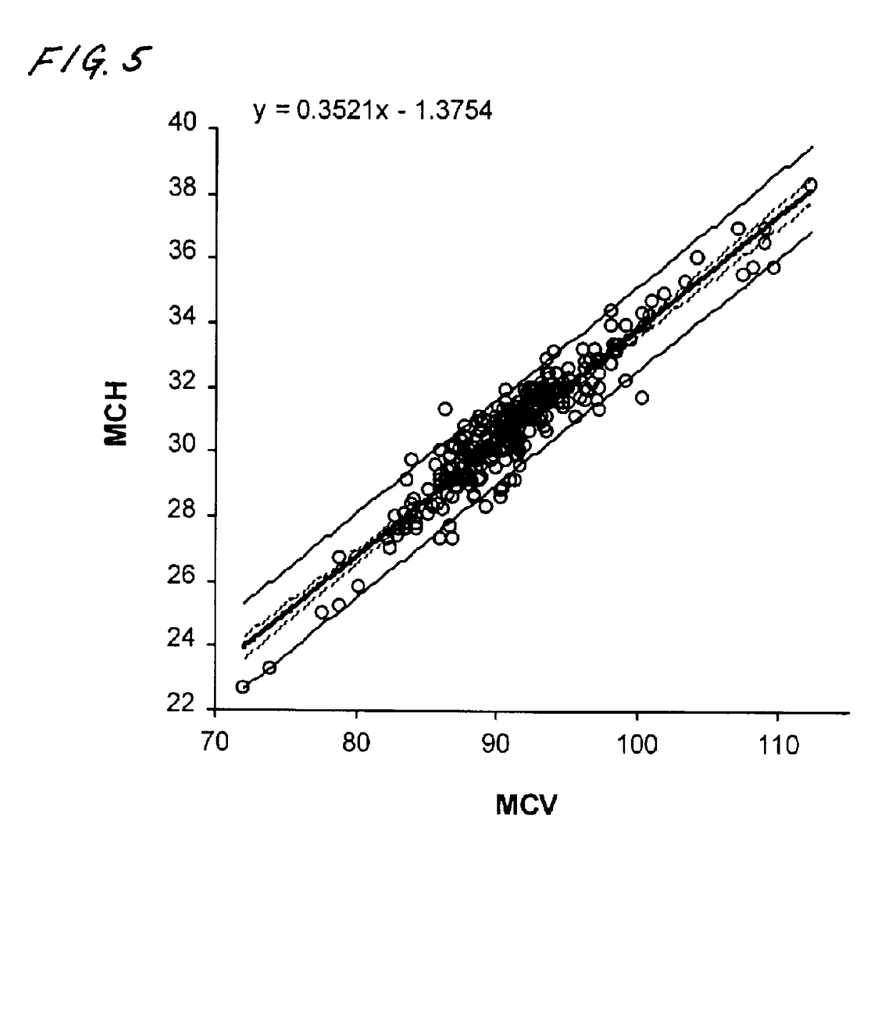
FIG. 5 is a graph showing how the values of MCH of samples of blood vary as a function of the values of MCV.

FIG. 1 shows the effect of storage on samples of blood that had been stored at room temperature for periods of up to 48 hours. The values of MCV were measured by means of a "CELL-DYN" 4000 hematology analyzer, commercially available from Abbott Laboratories. It is clear that upon being stored for a substantial period of time, a given sample of blood will exhibit an increase in the value of MCV measured. FIG. 2 shows that the initial values of MCH of given samples of blood are close to the values of MCH of those samples when those samples have been stored for periods of time of up to 48 hours. FIG. 5 shows that the value of MCH and the value of MCV of a sample of blood have a substantially linear relationship. Accordingly, the slope of the graph in FIG. 5 indicates the mean cell hemoglobin concentration of the sample, or MCHC.

Figure 4:
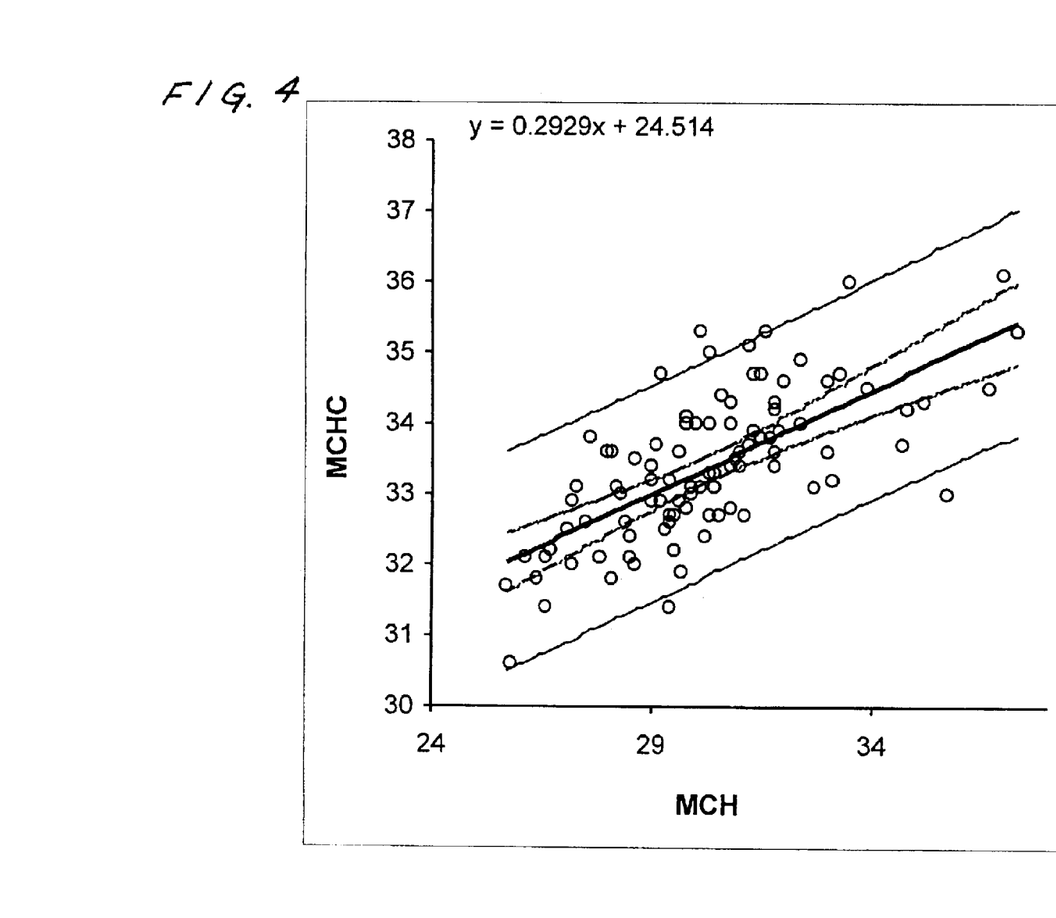
FIG. 4 is a graph showing how the values of MCHC of samples of blood vary as a function of the values of MCH.

The value of MCHC for the human population is typically about 33.3 g/dl. Accordingly, the calculated value of MCV is equal to the measured value of MCH divided by 33.3. Although this simple mathematical relationship can be used by itself to calculate the initial value of MCV of an aged sample of blood, the use of this mathematical relationship alone is flawed because the value of MCHC is not constant over a period of time relative to the value of MCH. This finding is depicted in FIG. 4, which shows the relationship between MCH and MCHC. Thus, as the value of MCH decreases, it would be expected that the value of MCHC would also decrease somewhat. In the absence of an additional correction, estimation of the initial value of MCV of a sample of blood by means of the value of MCH alone would tend to either overestimate or underestimate the value of MCV at the extremes of the measurement range, i.e., less than 27 pg MCH at the lower end of the measurement range and greater than 35 pg MCH at the upper end of the measurement range.

Knowledge of the typical relationship between the value of MCH and the value of MCHC for a fresh sample of blood allows one to determine the theoretical value of MCHC for a fresh sample of blood. In turn, the theoretical value of MCHC for a sample of blood can then be compared with the value of MCHC determined for a sample of blood and then used to calculate the theoretical value of MCV for a fresh sample of blood.

Based upon the measured value of MCH of a sample of blood, a calculated value of MCHC for the sample of blood can be derived via the following set of relationships:

$$\text{calculated value of } MCHC = a \times (\text{measured value of } MCH) + b \quad (1)$$

where "a" represents a constant and "b" represents a constant and "a" and "b" are derived from the regression relationship of MCH as a function of MCHC.

The values of "a" and "b" are derived by determining the relationship between the calculated value of MCHC and the measured value of MCH for a large number of fresh samples (e.g., fresh samples from about 100 patients) processed on a well-characterized and well-calibrated analytical instrument. The number of fresh samples required for the derivation of "a" and "b" should be sufficient to provide results that are deemed reliable from a statistical standpoint. For a typical automated hematology analyzer, the number of fresh samples required for determination of constants "a" and "b" is preferably at least about 50, more preferably at least about 100, and most preferably more than about 200.

$$\text{theoretical value of } MCV \text{ for a fresh sample} = (\text{measured value of } MCHC \text{ divided by the calculated value of } MCHC) \times (\text{measured value of } MCV) \quad (2)$$

It should be recognized that because the value of MCH and the value of MCHC are determined mathematically, there are numerous ways of calculating the value of MCV. The derivation shown previously is merely one example.

Figure 3:
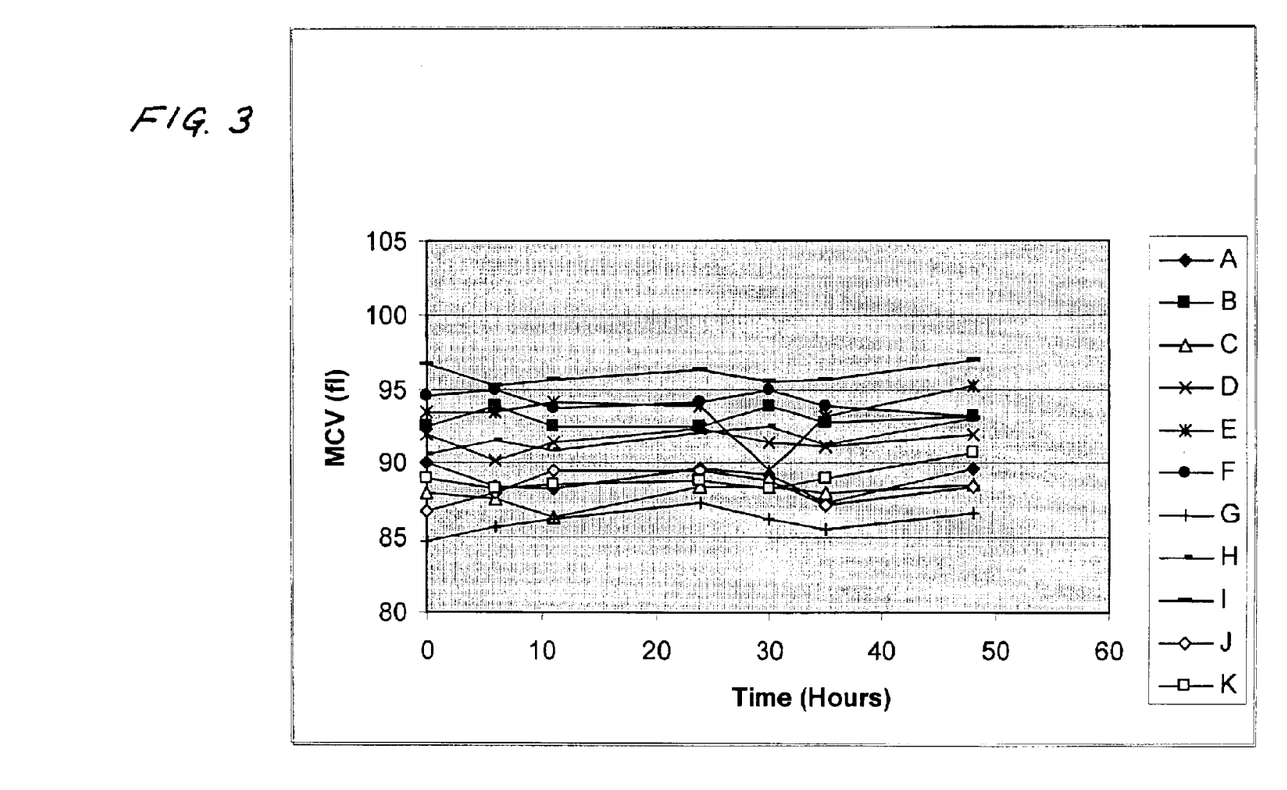
FIG. 3 a graph showing how the values of MCV of samples of blood at given times, calculated by the method of this invention, change as a function of time at room temperature.

The results of a typical calculation are shown in FIG. 3. For the set of data illustrated, the value of the constant "a" is 0.2929 and the value of the constant "b" is 24.514. FIG. 3 shows that for samples stored at room temperature for up to 48 hours, the calculated value of MCV remains substantially constant. In contrast, FIG. 1 shows that the measured values of MCV for the same samples show that the measured value of MCV increases as a function of time.

Figure 6A:
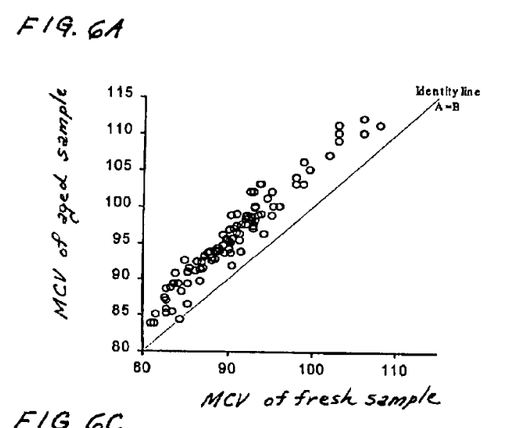
FIG. 6A is a graph showing how the values of MCV of samples of blood determined 24 hours after the samples were drawn compare to the values of MCV determined initially.
Figure 6B:
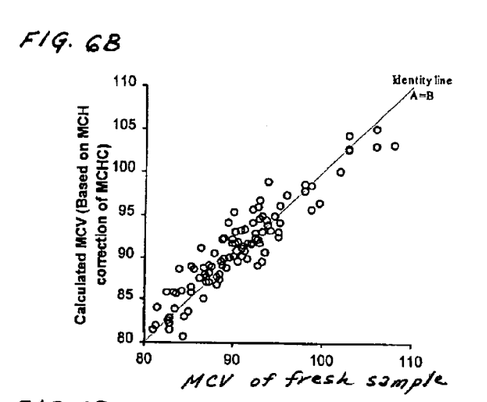
FIG. 6B is a graph showing how the initial values of MCV of samples of blood, calculated by the method of this invention, compare to the values of MCV determined initially.
Figure 6C:
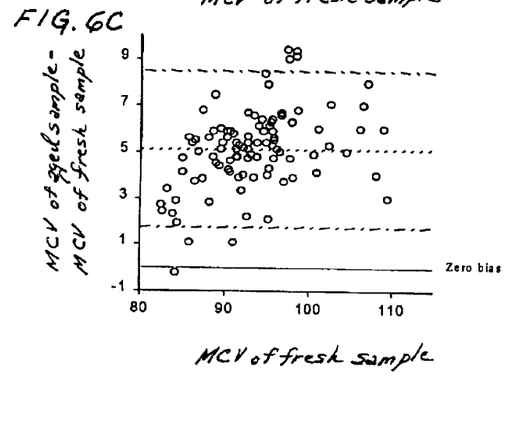
FIG. 6C is a plot showing the difference between (a) the values of MCV of samples of blood determined initially and (b) the values of MCV determined after the samples were aged for 24 hours as a function of the values of MCV determined initially.
Figure 6D:
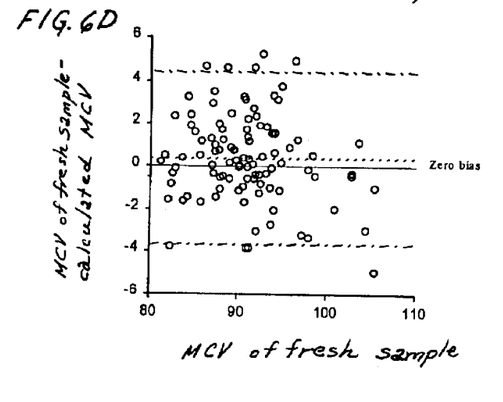
FIG. 6D is a plot showing the difference between (a) the values of MCV of samples of blood determined initially and (b) the initial values of MCV, calculated by the method of this invention, after the samples were aged for 24 hours as a function of the values of MCV determined initially.

Confirmation of the validity of the method of this invention for a large number of samples is shown in FIGS. 6A, 6B, 6C, and 6D. The number of samples in the set was 100. These figures compare the initial value of MCV of the samples with (1) the value of MCV of the samples actually measured after 24 hours and (2) the value of MCV of the samples after 24 hours, as calculated by the method of this invention. FIGS. 6A, 6B, 6C, and 6D show that the method of this invention can be used to more accurately determine the initial value of MCV of a sample that has aged upon storage. More particularly, the data in FIGS. 6B and 6D show that the method of this invention substantially eliminates the bias that is introduced by the use of aged samples in the determination of the initial value of MCV of a sample of blood.

The relationship between the values of MCH and MCHC can be established for a given hematology instrument. The relationship can be derived by means of data collected from fresh samples processed by means of properly calibrated instruments.

The following non-limiting examples further illustrate the method of this invention.

EXAMPLE 1

In the following example, the "CELL-DYN" 4000 hematology analyzer, commercially available from Abbott Laboratories, was used for the generation of the data. One hundred (100) samples of blood were used to establish the regression relationship between the value of MCH and the value of MCHC. Conventional least squares linear regression was used to derive the slope (constant "a") and the y-intercept (constant "b"), which constants will vary from instrument model to instrument model. In the linear regression analysis shown in FIG. 4, the constant "a" is 0.2929 and the constant "b" is 24.514. Consequently, if the value of MCH of the sample of blood were 30 pg, the value of MCV measured were 100 fl, and the value of MCHC measured were 30 g/dl, then:

Calculated Value of $MCHC = 30 \times 0.2929 + 24.514 = 33.3$ g/dl

Theoretical value of $MCV = (30/33.3) \times 100 = 90.1$ fl

Theoretical value of $MCV = (30 \times 100)/(30 \times 0.2929) + 24.524 = 90.1$ fl In this example, a value of MCV of 100 fl would be corrected by the method of this invention to a value of MCV of 90.1 fl.

EXAMPLES 2–5

In these examples, the values of MCV measured after the samples were stored for 24 hours at room temperature and the initial values of MCV, as calculated by the method of this invention after the samples were stored for 24 hours at room temperature, were compared with the values of MCV measured prior to storage of the samples. Table 1 shows the results of the comparison for measurements made with four instruments commercially available from Abbott Laboratories.

TABLE 1

| | "CELL-DYN" 4000 | "CELL-DYN" 3700 | "CELL-DYN" 3200 | "CELL-DYN" 1200 |
|---|---|---|---|---|
| Change in value of MCV of samples observed after storage at 24 hours relative to initial value of MCV of samples observed (fl) | 5.11 | 3.0 | 4.0 | 6.08 |
| Standard deviation of change above (fl) | 1.71 | 1.45 | 1.39 | 1.90 |
| Change in value of MCV of samples calculated by method of this invention after storage at 24 hours relative to initial value of MCV of samples observed (fl) | 0.362 | 0.39 | 0.44 | 0.59 |
| Standard deviation of change above (fl) | 2.05 | 1.50 | 2.66 | 1.65 |

On a variety of "CELL-DYN" automated analyzers, the value of MCV calculated by the method of this invention more accurately reflected the value of MCV determined initially than did the value of MCV determined for samples stored for 24 hours at room temperature.

Various modifications and alterations of this invention will become apparent to those skilled in the art without departing from the scope and spirit of this invention, and it should be understood that this invention is not to be unduly limited to the illustrative embodiments set forth herein.

What is claimed is:

1. A method for calculating the value of MCV for a fresh sample of blood, where MCV represents eryhrocyte mean cell volume and fresh means that venipuncture to obtain the sample of blood has occurred less than four hours prior to the measurement of MCV, said method comprising the steps of:

(a) providing a sample of blood aged for at least 16 hours;
   (b) determining at least the following hematology parameters of the sample: MCV, MCH, where MCH represents erythrocyte mean cell hemoglobin, and MCHC, where MCHC represents erythrocyte mean cell hemoglobin concentration;
   (c) calculating the value of MCHC of said sample of blood that would have been expected for said sample when said sample was fresh, said value of MCHC that would have been expected for said sample of blood when said sample was fresh being derived from the value of MCH determined in step (b) by means of an equation derived from a regression relationship of MCH as a function of MCHC;
   (d) comparing said value of MCHC that would have been expected for said sample of blood when said sample of blood was fresh with the value of MCHC determined; and (e) correcting said value of MCV determined in step (b) in order to determine the value of MCV for the sample of blood when said sample was fresh, said correcting being performed by multiplying the value of MCV determined in step (b) by the ratio of the value of MCHC determined in step (b) to the calculated value of MCHC determined in step (c), wherein the calculated value of MCHC is equal to "a" times the value of MCH determined in step (b) plus "b", where "a" represents a constant and "b" represents a constant and "a" and "b" are derived from the regression relationship of MCH as a function of MCHC.

2. The method of claim 1, wherein said hematology parameters in step (b) are determined by means of an automated hematology analyzer.

3. The method of claim 1, wherein said value of MCHC calculated in step (c) is calculated by the relationship between the value of MCH and the value of MCHC determined in a plurality of subjects.

4. The method of claim 1, wherein said step of correcting the value of MCV determined in step (b) utilizes a linear equation.

* * * * *